United States Patent
Choi et al.

(10) Patent No.: US 9,163,113 B2
(45) Date of Patent: Oct. 20, 2015

(54) CYCLIC OLEFIN COMPOUND HAVING PHOTOREACTIVE GROUP AND PHOTOREACTIVE POLYMER

(75) Inventors: Dai-Seung Choi, Daejeon (KR); Sung-Ho Chun, Daejeon (KR); Young-Chul Won, Daejeon (KR); Dong-Woo Yoo, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 13/238,965

(22) Filed: Sep. 21, 2011

(65) Prior Publication Data

US 2012/0076953 A1    Mar. 29, 2012

(30) Foreign Application Priority Data

Sep. 27, 2010    (KR) .................. 10-2010-0093180

(51) Int. Cl.
*C09K 19/00* (2006.01)
*C08G 61/08* (2006.01)
*C07C 69/736* (2006.01)
*C07C 69/738* (2006.01)
*C07C 69/76* (2006.01)
(Continued)

(52) U.S. Cl.
CPC .............. *C08G 61/08* (2013.01); *C07C 69/736* (2013.01); *C07C 69/738* (2013.01); *C07C 69/76* (2013.01); *C08F 32/08* (2013.01); *C07C 2102/42* (2013.01); *C08G 2261/135* (2013.01); *C08G 2261/3324* (2013.01); *C08G 2261/418* (2013.01); *C08G 2261/76* (2013.01); *C08L 65/00* (2013.01); *Y10T 428/1005* (2015.01)

(58) Field of Classification Search
CPC .... C07C 69/736; C07C 69/738; C07C 69/76; C07C 2102/42; Y10T 428/10; Y10T 428/1005; G02F 1/133711; G02F 1/13378; G02F 1/133788; C08F 32/08; C08G 61/08; C08G 2261/76; C08G 2261/3324; C08G 2261/418
USPC ............ 428/1.1, 1.2, 1.25, 1.26; 349/96, 117, 349/123; 526/282, 256, 281, 283, 284, 331
See application file for complete search history.

(56) References Cited

U.S. PATENT DOCUMENTS

| 2006/0159865 A1 | 7/2006 | Kim et al. |
| 2010/0047481 A1 | 2/2010 | Choi et al. |
| 2010/0093955 A1* | 4/2010 | Choi et al. .................. 526/123.1 |

(Continued)

FOREIGN PATENT DOCUMENTS

| CN | 1659205 A | 8/2005 |
| CN | 1881020 A | 12/2006 |

(Continued)

OTHER PUBLICATIONS

Kumar et al. "Photopatterned electrochromic conjugated polymer films via precursor approach", Polymer, vol. 49, 2008, p. 3686-3692.

(Continued)

*Primary Examiner* — Ruiyun Zhang
(74) *Attorney, Agent, or Firm* — Dentons US LLP

(57) ABSTRACT

Disclosed herein is a novel cyclic olefin compound having a photoreactive group and a novel photoreactive polymer. The cyclic olefin compound is applicable to various photoreactions, such as of liquid crystal alignment films and can be preferably used as a precursor of different organic compounds or polymers.

11 Claims, 1 Drawing Sheet

(51) Int. Cl.
*C08F 32/08* (2006.01)
*C08L 65/00* (2006.01)

(56) References Cited

U.S. PATENT DOCUMENTS

| | | | |
|---|---|---|---|
| 2010/0121005 A1 | 5/2010 | Kim et al. | |
| 2010/0182547 A1 | 7/2010 | Ryu et al. | |
| 2011/0213048 A1* | 9/2011 | Yoo et al. ................ | 522/112 |

FOREIGN PATENT DOCUMENTS

| | | |
|---|---|---|
| CN | 101065342 A | 10/2007 |
| CN | 101098840 A | 1/2008 |
| CN | 100396756 A | 6/2008 |
| CN | 101558131 A | 10/2009 |
| CN | 101641389 A | 2/2010 |
| CN | 101671250 A | 3/2010 |
| EP | 1188746 | 3/2002 |
| EP | 2 390 690 A1 | 11/2011 |
| JP | 2001200018 | 7/2001 |
| JP | 2003-306468 | 10/2003 |
| JP | 2006085098 | 3/2006 |
| JP | 2006104175 | 4/2006 |
| JP | 2006350347 | 12/2006 |
| JP | 2008503790 | 2/2008 |
| JP | 2010164975 A | 7/2010 |
| JP | 2010522253 | 7/2010 |
| JP | 2010522253 A | 7/2010 |
| JP | 2011510345 A | 3/2011 |
| JP | 2011511957 A | 4/2011 |
| JP | 2011514542 A | 5/2011 |
| JP | 2012515228 | 7/2012 |
| JP | 2013525566 | 6/2013 |
| JP | 2013525590 | 6/2013 |
| KR | 10-2004-0099406 A | 11/2004 |
| KR | 10-2008-0086409 A | 9/2008 |
| KR | 10-2008-0095207 A | 10/2008 |
| KR | 10-2009-0047720 A | 5/2009 |
| KR | 1020090047720 A * | 5/2009 |
| KR | 2009-0079842 | 7/2009 |
| KR | 2009-0079844 | 7/2009 |
| KR | 2010-0021751 | 2/2010 |
| KR | 10-2010-0083103 A | 7/2010 |
| KR | 10-1195186 | 10/2012 |
| WO | WO 2007/142458 | 12/2007 |
| WO | WO 2009/091225 | 7/2009 |
| WO | 2010080010 | 7/2010 |

OTHER PUBLICATIONS

Dyaduysha et al. "Peculiarity of an Oblique Liquid Crystal Alignment Induced by a Photosensitive Orientant", Japan Journal of Applied Physics, vol. 34, pp. L 1000-L 1002, Part 2, No. 8A, Aug. 1, 1995.

Schadt et al. "Surface-Induced parallel Alignment of Liquid Crystals by Linearly Polymerized Photopolymers", Japan Journal of Applied Physics, vol. 31, pp. 2155-2164, Part 1, No. 7, Jul. 1992.

* cited by examiner

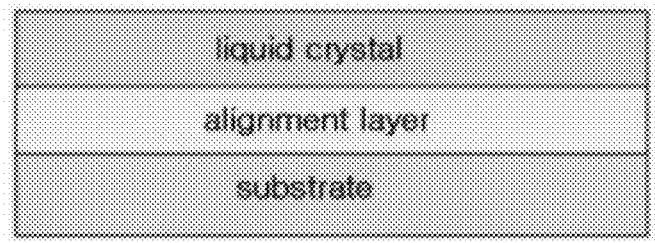

CYCLIC OLEFIN COMPOUND HAVING PHOTOREACTIVE GROUP AND PHOTOREACTIVE POLYMER

This application claims the benefit of Korean Patent Application No. 10-2010-0093180, filed on Sep. 27, 2010, which is hereby incorporated by reference in its entirety for all purposes as if fully set forth herein.

BACKGROUND OF THE INVENTION

1. Field of the Invention

The present invention relates to a novel cyclic olefin compound having a photoreactive group, and a novel photoreactive polymer and, more particularly, to a novel cyclic olefin compound having a photoreactive group and a photoreactive polymer prepared from the same that are applicable to various photoreactions, such as of liquid crystal alignment films, and can also be preferably used as precursors of different organic compounds or polymers.

2. Background Art

Recently, a variety of photoreactive compounds or polymers have been used in a wide range of optical applications, such as thin film transistor liquid crystal display (TFT-LCD), photoresist, and so forth.

TFT-LCDs, for example, have an alignment film underlying a liquid crystal film so as to use liquid crystals as optical switches. Recently, photoreactive polymers or the like are included in the alignment film to employ UV-based photo-alignment.

The term "photo-alignment" as used herein refers to a mechanism that the functional groups (photoreactors) of a defined photoreactive polymer causes photoreactions by a linearly polarized UV exposure, during which the polymer main chain is aligned in a defined direction, bringing about liquid crystal alignment.

For more effective photo-alignment to occur, the photoreactive polymer contained in the alignment film is required to cause good interactions with the molecules in the liquid crystal film and furthermore to possess a good photoreactivity.

With a gradual increase in the usage of photoreactive compounds or polymers in a wider variety of applications, there is a demand for various photoreactive compounds or polymers that have a high photoreactivity to more different types of light (e.g., omnidirectional polarized UV, UV of different wavelengths, etc.).

However, most of the existing photoreactive polymers do not have a good photoreactivity or cause enough interactions with liquid crystal molecules. Moreover, the development of photoreactive polymers with a good photoreactivity to various types of lights remains to be desired.

SUMMARY OF THE INVENTION

The present invention provides a novel cyclic olefin compound having a photoreactive group that is applicable to various photoreactions, such as of a liquid crystal alignment film, and can also be preferably used as a precursor of various organic compounds or polymers.

Further, the present invention provides a photoreactive polymer that allows easy control of photoreactivity to various types of lights and can be used for an alignment film or the like to achieve enhanced interactions with liquid crystal molecules and good photoreactivity.

Also, the present invention provides an alignment film comprising the photoreactive polymer.

The present invention provides a cyclic olefin compound having a photoreactive group as represented by the following formula 1:

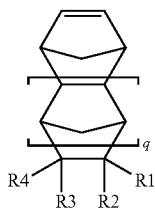

[Formula 1]

In the formula 1, q is an integer from 0 to 4; and at least one of R1, R2, R3 and R4 is a radical represented by the following formula 1a.

Among the R1 to R4, the remainders other than the radical of the formula 1a are the same as or different from one another and independently selected from the group consisting of hydrogen; halogen; substituted or unsubstituted linear or branched alkyl having 1 to 20 carbon atoms; substituted or unsubstituted linear or branched alkenyl having 2 to 20 carbon atoms; substituted or unsubstituted linear or branched alkynyl having 2 to 20 carbon atoms; substituted or unsubstituted cycloalkyl having 3 to 12 carbon atoms; substituted or unsubstituted aryl having 6 to 40 carbon atoms; substituted or unsubstituted arylalkyl having 5 to 12 carbon atoms; and a polar functional group comprising at least one of oxygen, nitrogen, phosphor, sulfur, silicon, and boron.

When the R1 to R4 are not hydrogen, halogen, or a polar functional group, at least one of a R1 and R2 coordination and a R3 and R4 coordination is bonded to each other to form an alkylidene group having 1 to 10 carbon atoms; or R1 or R2 is bonded to either R3 or R4 to form a saturated or unsaturated aliphatic ring having 4 to 12 carbon atoms or an aromatic ring having 6 to 24 carbon atoms.

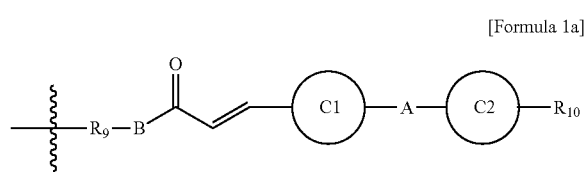

[Formula 1a]

In the formula 1a,

A is selected from the group consisting of oxygen, sulfur, —NH—, substituted or unsubstituted alkylene having 1 to 20 carbon atoms, carbonyl, —(O═)C—O—, —O—C(═O)—, —CONH—, and substituted or unsubstituted arylene having 6 to 40 carbon atoms;

B is chemical bond, oxygen, sulfur, —NH—, or 1,4-phenylene;

R9 is selected from the group consisting of chemical bond, substituted or unsubstituted alkylene having 1 to 20 carbon atoms, substituted or unsubstituted akenylene having 2 to 20 carbon atoms, substituted or unsubstituted cycloalkylene having 3 to 12 carbon atoms, substituted or unsubstituted arylene having 6 to 40 carbon atoms, substituted or unsubstituted arylalkylene having 7 to 15 carbon atoms, and substituted or unsubstituted alkynylene having 2 to 20 carbon atoms;

C1 is C6-C40 arylene unsubstituted or substituted with at least one functional group selected from the group consisting of halogen, cyano, and nitro; C7-C15 arylalkylene unsubstituted or substituted with at least one functional group selected from halogen, cyano, and nitro; or C4-C40 heteroarylene comprising a heteroelement in Group 14, 15 or 16;

C2 is C6-C40 arylene unsubstituted or substituted with at least one functional group selected from the group consisting of halogen, cyano, and nitro; or C4-C40 heteroarylene comprising a heteroelement in Group 14, 15 or 16; and R10 is selected from the group consisting of hydrogen; halogen; cyano; nitro; —NCS; substituted or unsubstituted linear or branched alkyl having 1 to 20 carbon atoms; substituted or unsubstituted alkoxy having 1 to 20 carbon atoms; substituted or unsubstituted aryloxy having 6 to 30 carbon atoms; and substituted or unsubstituted aryl having 6 to 40 carbon atoms.

The present invention also provides a photoreactive polymer comprising a repeating unit represented by the following formula 2a or 2b:

[Formula 2a]

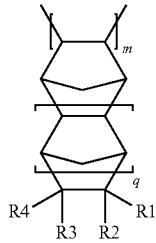

[Formula 2b]

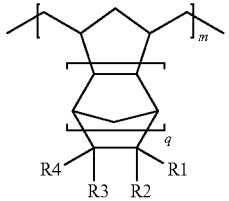

In the formula 2a or 2b, independently, m is 50 to 5,000; and q, R1, R2, R3 and R4 are as defined in the formula 1.

The present invention also provides an alignment film comprising the photoreactive polymer.

The present invention also provides a liquid crystal retardation film comprising the alignment film, and a liquid crystal film overlying the alignment film.

The present invention also provides a display device comprising the alignment film.

The cyclic olefin compound of the present invention may have a photoreactive group, such as a cinnamate or chalcone structure, depending on the structure of the formula 1a. Accordingly, the existence of the photoreactive group realizes the possession of good photoreactivity, which allows the cyclic olefin compound applicable to various photoreactions, such as of a liquid crystal alignment film or the like, and preferably used as a precursor of various organic compounds or polymers.

Further, the cyclic olefin compound may have the photoreactive group, such as a cinnamate or chalcone structure, additionally substituted with aromatic rings (C2). Typically, liquid crystal molecules have aromatic rings. With aromatic rings (C2) as additional substituents, the cyclic olefin compound or the photoreactive polymer obtained from the cyclic olefin compound is enabled to have enhanced interactions with the liquid crystal molecules, thereby bringing about photo-alignment more effectively.

In addition, the structure of the formula 1a of the cyclic olefin compound can be modified to provide different photoreactive compounds or polymers with high photoreactivity to different types of lights.

BRIEF DESCRIPTION OF THE DRAWINGS

FIG. 1 is a schematic diagram showing an exemplary structure of a general alignment film.

DETAILED DESCRIPTION OF THE PREFERRED EMBODIMENT

Hereinafter, a detailed description will be given as to a cyclic olefin compound having a photoreactive group, a photoreactive polymer, and an alignment film according to the preferred embodiments of the present invention.

In accordance with a preferred embodiment of the present invention, there is provided a cyclic olefin compound having a photoreactive group as represented by the following formula 1:

[Formula 1]

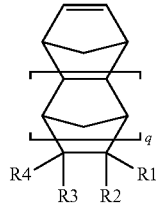

In the formula 1,
q is an integer from 0 to 4; and
at least one of R1, R2, R3 and R4 is a radical represented by the following formula 1a.

Among the R1 to R4, the remainders other than the radical of the formula 1a are the same as or different from one another and independently selected from the group consisting of hydrogen; halogen; substituted or unsubstituted linear or branched alkyl having 1 to 20 carbon atoms; substituted or unsubstituted linear or branched alkenyl having 2 to 20 carbon atoms; substituted or unsubstituted linear or branched alkynyl having 2 to 20 carbon atoms; substituted or unsubstituted cycloalkyl having 3 to 12 carbon atoms; substituted or unsubstituted aryl having 6 to 40 carbon atoms; substituted or unsubstituted arylalkyl having 5 to 12 carbon atoms; and a polar functional group comprising at least one of oxygen, nitrogen, phosphor, sulfur, silicon, and boron.

When the R1 to R4 are not hydrogen, halogen, or a polar functional group, at least one of a R1 and R2 coordination and a R3 and R4 coordination is bonded to each other to form an alkylidene group having 1 to 10 carbon atoms, or R1 or R2 is bonded to either R3 or R4 to form a saturated or unsaturated aliphatic ring having 4 to 12 carbon atoms or an aromatic ring having 6 to 24 carbon atoms.

[Formula 1a]

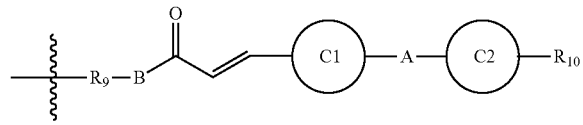

In the formula 1a,
A is selected from the group consisting of oxygen, sulfur, —NH—, substituted or unsubstituted alkylene having 1 to 20 carbon atoms, carbonyl, —(O═)C—O—, —O—C(═O)—, —CONH—, and substituted or unsubstituted arylene having 6 to 40 carbon atoms;

B is chemical bond, oxygen, sulfur, —NH—, or 1,4-phenylene;

R9 is selected from the group consisting of chemical bond, substituted or unsubstituted alkylene having 1 to 20 carbon atoms, substituted or unsubstituted akenylene having 2 to 20 carbon atoms, substituted or unsubstituted cycloalkylene having 3 to 12 carbon atoms, substituted or unsubstituted arylene having 6 to 40 carbon atoms, substituted or unsubstituted arylalkylene having 7 to 15 carbon atoms, and substituted or unsubstituted alkynylene having 2 to 20 carbon atoms;

C1 is C6-C40 arylene unsubstituted or substituted with at least one functional group selected from the group consisting of halogen, cyano, and nitro; C7-c15 arylalkylene unsubstituted or substituted with at least one functional group selected from halogen, cyano, and nitro; or C4-C40 heteroarylene comprising a heteroelement in Group 14, 15 or 16;

C2 is C6-C40 arylene unsubstituted or substituted with at least one functional group selected from the group consisting of halogen, cyano, and nitro; or C4-C40 heteroarylene comprising a heteroelement in Group 14, 15 or 16; and R10 is selected from the group consisting of hydrogen; halogen; cyano; nitro; —NCS; substituted or unsubstituted linear or branched alkyl having 1 to 20 carbon atoms; substituted or unsubstituted alkoxy having 1 to 20 carbon atoms; substituted or unsubstituted aryloxy having 6 to 30 carbon atoms; and substituted or unsubstituted aryl having 6 to 40 carbon atoms.

Such a compound has a chemical structure in which a photoreactive group (formula 1a) such as a cinnamate or chalcone structure is introduced in a cyclic olefin structure capable of being used as a precursor of different compounds or as a monomer of polymers. Such a chemical structure having a photoreactive group enables the cyclic olefin compound of the formula 1 used as a photoreactive compound in itself.

The structural characteristic of the cyclic olefin compound applicable as a precursor or the like makes possible preparation of various compounds or polymers from the cyclic olefin compound. Such compounds or polymers as prepared from the cyclic olefin compound are endowed with a good photoreactivity due to the existence of the photoreactive groups. Accordingly, the cyclic olefin compound can be used to prepare a variety of photoreactive compounds or polymers applicable to a wide range of optical applications.

The cyclic olefin compound may have a chemical structure in which an aromatic ring substituent (C2) is additionally bonded to the photoreactive group such as a cinnamate or chalcone structure via a specific functional group A. Typically, liquid crystal molecules have aromatic rings. The additional aromatic ring substituent (C2) bonded to the cyclic olefin compound endows the cyclic olefin compound or the photoreactive polymer obtained from the cyclic olefin compound with enhanced interactions with the liquid crystal molecules, thereby bringing about photo-alignment more effectively. Accordingly, the cyclic olefin compound and the photoreactive polymer obtained from the cyclic olefin compound can be preferably used in liquid crystal alignment films or the like to have enhanced interactions with the liquid crystal molecules and good photoreactivity.

In addition, the structure of the formula 1a of the cyclic olefin compound, particularly, the type of the additional aromatic ring substituent (C2) may be modified with different arylenes or heteroarylenes to easily regulate the photoreactivity of the cyclic olefin compound or the photoreactive polymer obtained from the cyclic olefin compound. Hence the cyclic olefin compound can be used to prepare various photoreactive compounds or polymers having a good photoreactivity to different types of lights.

Hereinafter, a further detailed description will be given as to the cyclic olefin compound and the photoreactive polymer obtained from the same.

In the cyclic olefin compound, a polar functional group used as a substituent for the R1 to R4, that is, a polar functional group comprising at least one of oxygen, nitrogen, phosphor, sulfur, silicon, and boron may be selected from the group consisting of the following functional groups, or otherwise comprise at least one of oxygen, nitrogen, phosphor, sulfur, silicon, and boron:

—OR$_6$, —OC(O)OR$_6$, —R$_5$OC(O)OR$_6$, —C(O)OR$_6$, —R$_5$C(O)OR$_6$, —C(O)R$_6$, —R$_5$C(O)R$_6$, —OC(O)R$_6$, —R$_5$OC(O)R$_6$, —(R$_5$O)$_p$—OR$_6$, —(OR$_5$)$_p$—OR$_6$, —C(O)—O—C(O)R$_6$, —R$_5$C(O)—O—C(O)R$_6$, —SR$_6$, —R$_5$SR$_6$, —SSR$_6$, —R$_5$SSR$_6$, —S(═O)R$_6$, —R$_5$S(═O)R$_6$, —R$_5$C(═S)R$_6$—, —R$_5$C(═S)SR$_6$, —R$_5$SO$_3$R$_6$, —SO$_3$R$_6$, —R$_5$N═C═S, —N═C═S, —NCO, —R$_5$—NCO, —CN, —R$_5$CN, —NNC(═S)R$_6$, —R$_5$NNC(═S)R$_6$, —NO$_2$, —R$_5$NO$_2$,

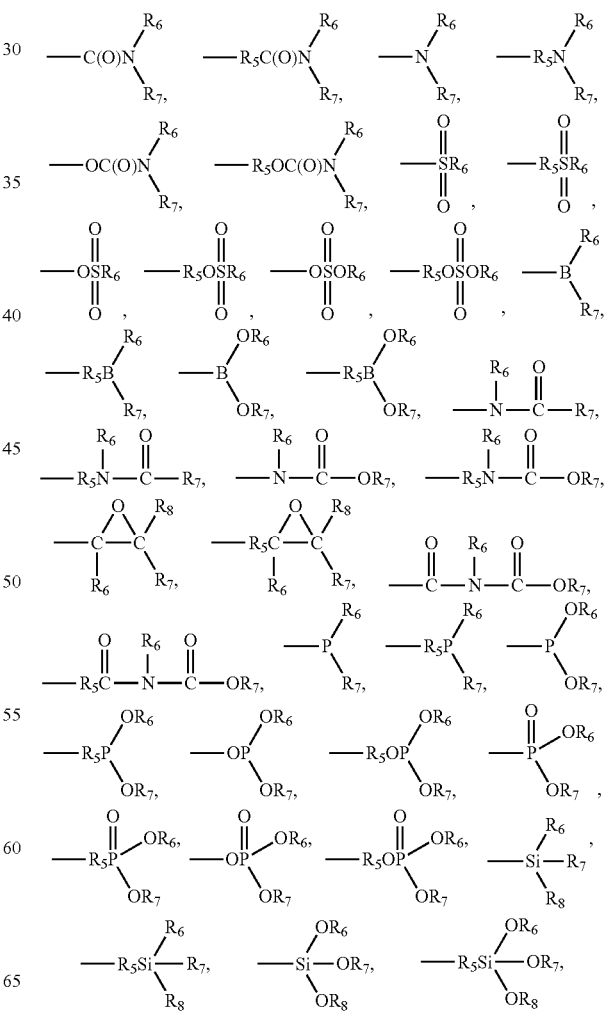

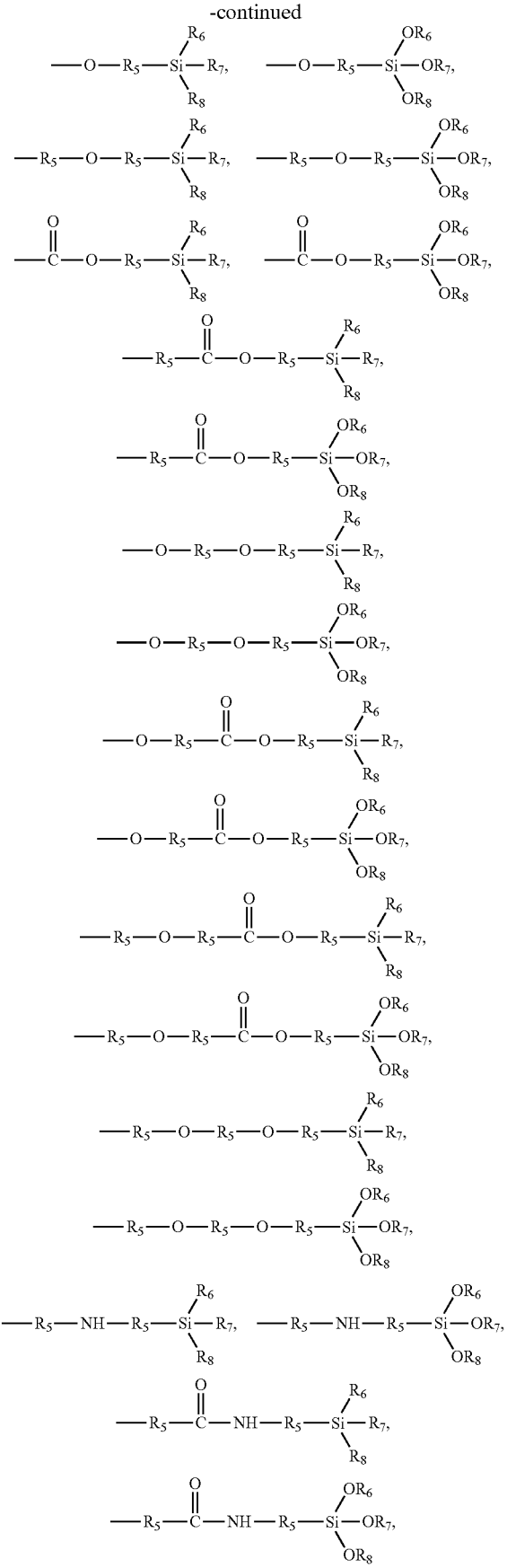

In the polar functional group, p is independently an integer from 1 to 10;

R5 is substituted or unsubstituted linear or branched alkylene having 1 to 20 carbon atoms; substituted or unsubstituted linear or branched alkenylene having 2 to 20 carbon atoms; substituted or unsubstituted linear or branched alkynylene having 2 to 20 carbon atoms; substituted or unsubstituted cycloalkylene having 3 to 12 carbon atoms; substituted or unsubstituted arylene having 6 to 40 carbon atoms; substituted or unsubstituted carbonyloxylene having 1 to 20 carbon atoms; or substituted or unsubstituted alkoxylene having 1 to 20 carbon atoms; and R6, R7 and R8 are independently selected from the group consisting of hydrogen; halogen; substituted or unsubstituted linear or branched alkyl having 1 to 20 carbon atoms; substituted or unsubstituted linear or branched alkenyl having 2 to 20 carbon atoms; substituted or unsubstituted linear or branched alkynyl having 2 to 20 carbon atoms; substituted or unsubstituted cycloalkyl having 3 to 12 carbon atoms; substituted or unsubstituted aryl having 6 to 40 carbon atoms; substituted or unsubstituted alkoxy having 1 to 20 carbon atoms; and substituted or unsubstituted carbonyloxy having 1 to 20 carbon atoms.

In the cyclic olefin compound, the C1 is C6-C40 arylene (e.g., substituted or unsubstituted phenylene, 1,4- or 2,6-naphthylene, etc.) unsubstituted or substituted with at least one functional group selected from the group consisting of halogen, cyano, and nitro; C7-C15 arylalkylene unsubstituted or substituted with at least one functional group selected from halogen, cyano, and nitro; or C4-C40 heteroarylene (e.g., 2,5-thiophenediyl, 2,5-furanylene, etc.) comprising a heteroelement in Group 14, 15 or 16.

The C2 bonded to the C1 via a specific functional group A may be C6-C40 arylene (e.g., substituted or unsubstituted phenylene, 1,4- or 2,6-naphthylene, etc.) unsubstituted or substituted with at least one functional group selected from the group consisting of halogen, cyano, and nitro; or C4-C40 heteroarylene (e.g., 2,5-thiophenediyl, 2,5-furanylene, etc.) comprising a heteroelement in Group 14, 15 or 16.

In the above-described structure of the cyclic olefin compound, the respective substituents are defined as follows:

The term "alkyl" as used herein refers to a monovalent linear or branched saturated hydrocarbon portion having 1 to 20 carbon atoms, preferably 1 to 10 carbon atoms, more preferably 1 to 6 carbon atoms. The alkyl group inclusively refers to an alkyl group unsubstituted or additionally substituted with defined substituents, as will be described later. The examples of the alkyl group may include methyl, ethyl, propyl, 2-propyl, n-butyl, iso-butyl, tert-butyl, pentyl, hexyl, dodecyl, fluoromethyl, difluoromethyl, trifluoromethyl, chloromethyl, dichloromethyl, trichloromethyl, iodomethyl, bromomethyl, etc.

The term "alkenyl" as used herein refers to a monovalent linear or branched hydrocarbon portion having 2 to 20 carbon atoms, preferably 2 to 10 carbon atoms, more preferably 2 to 6 carbon atoms with at least one carbon-carbon double bond. The alkenyl group may form a bonding through carbon atoms including a carbon-carbon double bond or through saturated carbon atoms. The alkenyl group inclusively refers to an alkenyl group unsubstituted or additionally substituted with a specific substituent, as will be described later. The examples of the alkenyl group may include ethenyl, 1-propenyl, 2-propenyl, 2-butenyl, 3-butenyl, pentenyl, 5-hexenyl, dodecenyl, etc.

The term "cycloalkyl" as used herein refers to a monovalent saturated or unsaturated mono-, bi- or tri-cyclic non-aromatic hydrocarbon portion having 3 to 12 ring-carbon atoms. The cycloalkyl group inclusively refers to a cycloalkyl group additionally substituted with a specific substituent, as will be described later. The examples of the cycloalkyl group may include cyclopropyl, cyclobutyl, cyclopentyl, cyclopentenyl, cyclohexyl, cyclohexenyl, cycloheptyl, cyclooctyl, decahydronaphthalenyl, adamantyl, norbornyl (i.e., bicyclo[2,2,1]hept-5-enyl), etc.

The term "aryl" as used herein refers to a monovalent mono-, bi- or tri-cyclic aromatic hydrocarbon portion having 6 to 40 ring-carbon atoms, preferably 6 to 12 ring-carbon atoms. The aryl group inclusively refers to an aryl group additionally substituted with a specific substituent, as will be described later. The examples of the aryl may include phenyl, naphthalenyl, fluorenyl, etc.

The term "alkoxyaryl" as used herein refers to the above-defined aryl group in which at least one hydrogen atom is substituted by an alkoxy group. The examples of the alkoxyaryl group may include methoxyphenyl, ethoxyphenyl, propoxyphenyl, butoxyphenyl, pentoxyphenyl, hextoxyphenyl, heptoxy, octoxy, nanoxy, methoxybiphenyl, methoxynaphthalenyl, methoxyfluorenyl, methoxyanthracenyl, etc.

The term "arylalkyl" as used herein refers to the above-defined alkyl group in which at least one hydrogen atom is substituted by an aryl group. The arylalkyl group inclusively refers to an arylalkyl additionally substituted with a specific substituent, as will be described later. The examples of the arylalkyl may include benzyl, benzhydryl, trityl, etc.

The term "alkynyl" as used herein refers to a monovalent linear or branched hydrocarbon portion having 2 to 20 carbon atoms, preferably 2 to 10 carbon atoms, more preferably 2 to 6 carbon atoms with at least one carbon-carbon triple bond. The alkynyl group may form a bonding through carbon atoms including a carbon-carbon triple bond or through saturated carbon atoms. The alkynyl group inclusively refers to an alkynyl group additionally substituted with a specific substituent, as will be described later. The examples of the alkynyl group may include ethynyl, propynyl, or the like.

The term "alkylene" as used herein refers to a divalent linear or branched saturated hydrocarbon portion having 1 to 20 carbon atoms, preferably 1 to 10 carbon atoms, more preferably 1 to 6 carbon atoms. The alkylene group inclusively refers to an alkylene group additionally substituted with a specific substituent, as will be described later. The examples of the alkylene group may include methylene, ethylene, propylene, butylene, hexylene, or the like.

The term "alkenylene" as used herein refers to a divalent linear or branched hydrocarbon portion having 2 to 20 carbon atoms, preferably 2 to 10 carbon atoms, more preferably 2 to 6 carbon atoms with at least one carbon-carbon double bond. The alkenylene group may form a bonding through carbon atoms including a carbon-carbon double bond and/or through saturated carbon atoms. The alkenylene group inclusively refers to an alkenylene group additionally substituted with a specific substituent, as will be described later.

The term "cycloalkylene" as used herein refers to a divalent saturated or unsaturated mono-, bi- or tri-cyclic non-aromatic hydrocarbon portion having 3 to 12 ring-carbon atoms. The cycloalkylene group inclusively refers to a cycloalkylene group additionally substituted with a specific substituent, as will be described later. The examples of the cycloalkylene group may include cyclopropylene, cyclobutylene, or the like.

The term "arylene" as used herein refers to a divalent mono-, bi- or tri-cyclic aromatic hydrocarbon portion having 6 to 20 ring-carbon atoms, preferably 6 to 12 ring-carbon atoms. The arylene group inclusively refers to an arylene group additionally substituted with a specific substituent, as will be described later. The aromatic portion includes carbon atoms only. The examples of the arylene may include phenylene, or the like.

The term "arylalkylene" as used herein refers to a divalent portion of the above-defined alkyl group in which at least one hydrogen atom is substituted by an aryl group. The arylalkylene group inclusively refers to an arylalkylene group additionally substituted with a specific substituent, as will be described later. The examples of the arylalkylene group may include benzylene, or the like.

The term "alkynylene" as used herein refers to a divalent linear or branched hydrocarbon portion having 2 to 20 carbon atoms, preferably 2 to 10 carbon atoms, more preferably 2 to 6 carbon atoms with at least one carbon-carbon triple bond. The alkynylene group may form a bonding through carbon atoms including a carbon-carbon triple bond or through saturated carbon atoms. The alkynylene group inclusively refers to an alkynylene group additionally substituted with a specific substituent, as will be described later. The examples of the alkynylene group may include ethynylene, propynylene, or the like.

In the above description, the phrase "a substituent is substituted or unsubstituted" has an inclusive meaning that the substituent is or isn't additionally substituted with the substituent itself or another defined substituent. It not stated otherwise in this specification, the examples of the substituent used as an additional substituent for each substituent may include halogen, alkyl, alkenyl, alkynyl, haloalkyl, haloalkenyl, haloalkynyl, aryl, haloaryl, arylalkyl, haloarylalkyl, alkoxy, haloalkoxy, carbonyloxy, halocarbonyloxy, aryloxy, haloaryloxy, silyl, siloxy, or "a polar functional group including oxygen, nitrogen, phosphor, sulfur, silicon, or boron" as mentioned above.

The above-described cyclic olefin compound may be prepared by a typical method of introducing a defined substituent, more specifically, a photoreactive group of the formula 1a on a cyclic olefin compound such as a norbornene-based compound. The synthesis of the cyclic olefin compound involves, for example, a condensation reaction of a norbornene alkylol, such as norbornene methanol, and a carboxylic compound or an acyl chloride compound having a photoreactive group corresponding to the formula 1a. Otherwise, depending on the type of the photoreactive group of the formula 1a, any different method may be used to introduce the photoreactive group of the formula 1a and prepare the cyclic olefin compound.

In accordance with another embodiment of the present invention, there is provided a photoreactive polymer comprising a repeating unit of the following formula 2a or 2b:

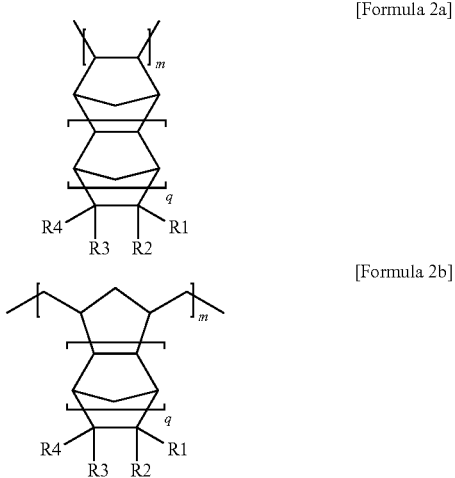

[Formula 2a]

[Formula 2b]

In the formulas 2a and 2b, independently, m is 50 to 5,000; and q, R1, R2, R3 and R4 are as defined above in the formula 1.

This photoreactive polymer, which comprises a repeating unit derived from the cyclic olefin compound, exhibits a good photoreactivity. With the structure of the formula 1a, particularly having an additional aromatic ring substituent (C2) via a specific functional group A, the photoreactive polymer is endowed with enhanced interactions with liquid crystal molecules and a good photoreactivity. Further, selection and modification of the aromatic ring substituent among different arylenes or heteroarylenes may allow the photoreactive polymer to have a good photoreactivity to different types of lights.

The photoreactive polymer comprises a norbornene-based repeating unit of the formula 2a or 2b as a main repeating unit. The norbornene-based repeating unit is structurally rigid, and the photoreactive polymer containing the norbornene-based repeating unit has a relatively high glass transition temperature Tg of about 300° C. or above, preferably about 300 to 350° C., consequently with a superior thermal stability to the existing known photoreactive polymers. Due to a structural characteristic that a photoreactive group is bonded to the norbornene repeating unit, the photoreactive polymer has the photoreactive group relatively free to move in the main chain, thereby achieving good alignment.

Hence the photoreactive polymer is preferably used for liquid crystal alignment films for photo-alignment and adopted in a wide range of optical applications.

The definitions of the respective substituents bonded to the photoreactive polymer are specified above in detail in regard to the formula 1 and will not be described any more.

The photoreactive polymer may comprise at least one repeating unit selected from the group consisting of the repeating units of the formula 2a or 2b, or also may be a copolymer further comprising another type of repeating units. The examples of the repeating unit may include any olefin-, acrylate- or cyclic-olefin-based repeating unit with or without a bonding to cinnamate-, chalcone- or azo-based photoreactive groups. The exemplary repeating units are disclosed in Korean Patent Laid-open Publication No. 2010-0021751.

To prevent a deterioration in good photoreactivity pertaining to the formula 2a or 2b, the photoreactive polymer may comprise at least about 50 mol %, more specifically about 50 to 100 mol %, preferably at least about 70 mol % of the repeating unit of the formula 2a or 2b.

The repeating unit of the formula 2a or 2b constituting the photoreactive polymer has a degree of polymerization in the range of about 50 to 5,000, preferably about 100 to 4,000, more preferably about 1,000 to 3,000. The photoreactive polymer has a weight average molecular weight of 10,000 to 1,000,000, preferably 20,000 to 500,000. The photoreactive polymer properly included in a coating composition for forming an alignment film provides the coating composition with good coating property and the alignment film formed from the coating composition with good liquid crystal alignment.

The photoreactive polymer may be endowed with photoreactivity upon exposure to a polarized light having a wavelength of about 150 to 450 nm, such as about 200 to 400 nm, more specifically about 250 to 350 nm. In particular, selection and modification of the aromatic ring substituent (C2) additionally bonded via a specific functional group A among different arylenes or heteroarylenes contributes to having good photoreactivity to different lights of a wide wavelength range and omnidirectional polarized lights.

In accordance with another embodiment of the present invention, there is provided a method for preparing the photoreactive polymer. An example of the preparation method comprises performing an addition polymerization reaction using a monomer represented by the formula 1 in the presence of a catalyst composition containing a precatalyst and a cocatalyst comprising a transition metal in Group 10:

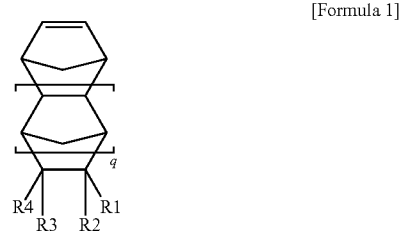

[Formula 1]

In the formula 1, q, R1, R2, R3 and R4 are as defined in the formula 2a.

The polymerization reaction may be carried out at a temperature of 10 to 200° C. The polymerization temperature below 10° C. lowers the polymerization activity, while the temperature above 200° C. undesirably causes a cleavage of the catalyst.

The cocatalyst comprises at least one selected from the group consisting of a first cocatalyst providing a Lewis base capable of forming a weak coordinate bond with the metal of the precatalyst; and a second cocatalyst providing a compound comprising a Group 15 electron donor ligand. Preferably, the cocatalyst may be a catalyst mixture comprising the first cocatalyst providing a Lewis base, and optionally the second cocatalyst providing a compound comprising a neutral Group 15 electron donor ligand.

The catalyst mixture may comprise, based on one mole of the precatalyst, 1 to 1,000 moles of the first cocatalyst and 1 to 1,000 moles of the second cocatalyst. The excessively low content of the first or second cocatalyst causes a failure to provide the catalyst activity enough, while an excess of the first or second cocatalyst deteriorates the catalyst activity.

The precatalyst comprising a Group 10 transition metal may be a compound having a Lewis base functional group that is readily leaving from the central transition metal by the first cocatalyst providing a Lewis base and participating in a Lewis acid-base reaction to help the central transition metal changed into a catalyst active species. The examples of the precatalyst include allylpalladium chloride dimer ($[(Allyl)Pd(Cl)]_2$), palladium(II) acetate (($CH_3CO_2)_2Pd$), palladium(II) acetylacetonate ($[CH_3COCH=C(O-)CH_3]_2Pd$), $NiBr(NP(CH_3)_3)_4$, $[PdCl(NB)O(CH_3)]_2$, or the like.

The first cocatalyst providing a Lewis base capable of forming a weak coordinate bond with the metal of the precatalyst may be a compound that readily reacts with a Lewis base to leave vacancies in the transition metal and forms a weak coordinate bond with a transition metal compound in order to stabilize the resultant transition metal; or a compound providing such a compound. The examples of the first cocatalyst may include borane (e.g., $B(C_6F_5)_3$), borate (e.g., dimethylanilinium tetrakis(pentafluorophenyl)borate), alkylaluminum (e.g., methylaluminoxane (MAO) or $Al(C_2H_5)_3$), transition metal halide (e.g., $AgSbF_6$), or the like.

The examples of the second cocatalyst that provides a compound comprising a neutral Group 15 electron donor ligand may include alkyl phosphine, cycloalkyl phosphine, or phenyl phosphine.

The first and second cocatalysts may be used separately, or used together to form a single salt compound used as a compound for activating the catalyst. For example, there may be a compound prepared as an ion pair of alkyl phosphine and a borane or borate compound.

The above-described method may be used to prepare a repeating unit of the formula 2a and a photoreactive polymer according to an embodiment comprising the repeating unit. In addition, as for a photoreactive polymer further comprising an olefin-, cyclic-olefin- or acrylate-based repeating unit, typical preparation methods are used for forming each of the corresponding repeating units, and the repeating units are then copolymerized with the repeating unit of the formula 2a prepared by the above-described method to form the photoreactive polymer.

On the other hand, a photoreactive polymer comprising a repeating unit of the formula 2a may be prepared according to another example of the preparation method. The another exemplary preparation method comprises performing a ring-opening polymerization using a monomer of the formula 1 in the presence of a catalyst composition containing a precatalyst comprising a transition metal in Group 4, 6 or 8 and a cocatalyst to form a repeating unit of the formula 2b. Alternatively, the photoreactive polymer comprising a repeating unit of the formula 2b may be prepared by a method that comprises performing a ring-opening polymerization reaction using norbornene methanol as a norbornene monomer in the presence of a catalyst composition containing a precatalyst comprising a transition metal in Group 4, 6 or 8 to form a ring-opened polymer with a 5-membered ring, and then introducing such a photoreactive group on the polymer to complete the photoreactive polymer. Here, the introduction of the photoreactive group may be achieved using a condensation reaction of the polymer with a carboxylate compound or an acyl chloride compound having a photoreactive group corresponding to the formula 1a.

The ring-opening polymerization step may involve hydrogenation of the double bond of the norbornene ring included in the monomer of the formula 1 to open the norbornene ring, simultaneously beginning a polymerization reaction to prepare a repeating unit of the formula 2b and a photoreactive polymer comprising the repeating unit.

The ring-opening polymerization may be carried out in the presence of a catalyst composition, which consists of a precatalyst comprising a transition metal in Group 4 (e.g., Ti, Zr, or Hf), Group 6 (e.g., Mo, or W) or Group 8 (e.g., Ru, or Os); a cocatalyst providing a Lewis base capable of forming a weak coordinate bond with the metal of the precatalyst; or optionally a neutral Group 15 or Group 16 activator for improving the activity of the metal in the precatalyst. In the presence of the catalyst composition, a linear alkene, such as 1-alkene, 2-alkene, etc., for molecular weight control is added in an amount of 1 to 100 mol % with respect to the monomer, and a polymerization reaction is carried out at a temperature of 10 to 200° C. Then, a catalyst comprising a transition metal in Group 4 (e.g., Ti, or Zr) or Groups 8 to 10 (e.g., Ru, Ni, or Pd) is added in an amount of 1 to 30 wt. % with respect to the monomer to catalyze a hydrogenation reaction on the double bond of the norbornene ring at 10 to 250° C.

The lower reaction temperature deteriorates the polymerization activity, and the higher reaction temperature results in a cleavage of the catalyst. The lower hydrogenation temperature deteriorates the reaction activity, while the excessively high hydrogenation temperature causes a cleavage of the catalyst.

The catalyst composition comprises one mole of a precatalyst comprising a transition metal in Group 4 (e.g., Ti, Zr, or Hf), Group 6 (e.g., Mo, or W) or Group 8 (e.g., Ru, or Os); 1 to 100,000 moles of a cocatalyst providing a Lewis base capable of forming a weak coordinate bond with the metal of the precatalyst; or optionally 1 to 100 moles of an activator comprising a neutral Group 15 or 16 element for improving the activity of the metal of the precatalyst.

The cocatalyst content less than one mole causes a failure in activation of the catalyst, and the cocatalyst content greater than 100,000 moles deteriorates the catalyst activity. The activator may be unnecessary depending on the type of the precatalyst. The activator content less than one mole ends up with a failure of the catalyst activation, while the activator content greater than 100 moles results in a lower molecular weight.

The hydrogenation reaction fails to occur when the content of the catalyst comprising a transition metal of Group 4 (e.g., Ti, or Zr) or Group 8, 9 or 10 (e.g., Ru, Ni, or Pd) for hydrogenation reaction is less than 1 wt. % with respect to the monomer. The catalyst content greater than 30 wt. % undesirably results in a discoloration of the polymer.

The precatalyst comprising a transition metal in Group 4 (e.g., Ti, Zr, or Hf), Group 6 (e.g., Mo, or W) or Group 8 (e.g., Ru, or Os) may refer to a transition metal compound, such as $TiCl_4$, $WCl_6$, $MoCl_5$, $RuCl_3$, or $ZrCl_4$, having a functional group that is readily leaving from the central transition metal by the first cocatalyst providing a Lewis base and participating in a Lewis acid-base reaction to help the central transition metal changed into a catalyst active species.

The examples of the cocatalyst providing a Lewis base capable of forming a weak coordinate bond with the metal of the precatalyst may include borane, such as $B((C_6F_5)_3$, or borate; or alkylaluminum, alkylaluminum halide or aluminum halide, such as methylaluminoxane (MAO), $Al(C_2H_5)_3$, or $Al(CH_3)Cl_2$. Here, aluminum may be replaced by a substituent, such as lithium, magnesium, germanium, lead, zinc, tin, silicon, or the like. In this manner, the cocatalyst is a compound that readily reacts with a Lewis base to provide vacancies in the transition metal and forms a weak coordinate bond with the transition metal compound in order to stabilize the produced transition metal; and a compound providing such a compound.

Depending on the type of the precatalyst, a polymerization activator is required or not. The examples of the activator comprising a neutral element in Group 15 or 16 may include water, methanol, ethanol, isopropyl alcohol, benzylalcohol, phenol, ethyl mercaptan, 2-chloroethanol, trimethylamine, triethylamine, pyridine, ethylene oxide, benzoyl peroxide, t-butyl peroxide, or the like.

The catalyst comprising a transition metal in Group 4 (e.g., Ti, or Zr) or Group 8, 9 or 10 (e.g., Ru, Ni, or Pd) used for hydrogenation reaction may be prepared as a homogeneous form miscible with a solvent, or as a metal complex catalyst impregnated on a particulate support. Preferably, the examples of the particulate support may include silica, titania, silica/chromia, silica/chromia/titania, silica/alumina, aluminum phosphate gel, silanized silica, silica hydrogel, montmorillonite clay, or zeolite.

The above-described method is used to prepare the repeating unit of the formula 2b and the photoreactive polymer of the embodiment comprising the repeating unit. As for the photoreactive polymer that further comprises an olefin-, cyclic-olefin- or acrylate-based repeating unit, the respective repeating units are first formed through the corresponding preparation methods and then copolymerized with a repeating unit of the formula 2b prepared by the above-described method to obtain the photoreactive polymer.

In accordance with another embodiment of the present invention, there is provided an alignment film comprising the above-described photoreactive polymer. The alignment film may be of a thin film form or an alignment film form. In accordance with further another embodiment of the present invention, there is provided a liquid crystal retardation film comprising the alignment film, and a liquid crystal film overlying the alignment film.

The alignment film and the liquid crystal retardation film may be prepared using known preparation methods with constituent components known to those skilled in the art, excepting that the photoreactive polymer is a photo-alignment polymer.

For example, the alignment film is prepared by mixing the photoreactive polymer with a binder resin and a photo-initiator, dissolving the mixture in an organic solvent to obtain a coating composition, applying the coating composition on a base, and then curing the coating composition by UV exposure.

Here, the binder resin may be an acrylate-based resin, more specifically, pentaerythritol triarylate, dipentaerythritol hexaacrylate, trimethylolpropane triacrylate, tris(2-acryloyloxyethyl)isocyanurate, or the like.

The photo-initiator may be any typical photo-initiator known to be applicable to alignment films without any limitations, such as, for example, Irgacure 907 or Irgacure 819.

The examples of the organic solvent may include toluene, anisole, chlorobenzene, dichloroethane, cyclohexane, cyclopentane, propylene glycol, methyl ether, acetate, or the like. Other organic solvent may also be used without any limitations, because the photoreactive norbornene-based copolymer has a very good solubility in various organic solvents.

In the coating composition, the content of the solid components comprising the binder resin and the photo-initiator may be in the range of 1 to 15 wt. %, preferably 10 to 15 wt. % for casting the alignment film as a film, or 1 to 5 wt. % for casting the alignment film as a thin film.

The alignment film may be formed, for example, on a support as shown in FIG. 1, or under the liquid crystal film to achieve liquid crystal alignment. Here, the base may be a cyclic polymer base, an acryl polymer base, or a cellulose polymer base. To form the alignment film, the coating composition is applied on the base through different methods, such as bar coating, spin coating, blade coating, etc. and then cured under UV exposure.

The UV curing may cause photo-alignment, in which step a polarized UV radiation in the wavelength range of about 150 to 450 nm is applied to bring about alignment. Here, the exposure intensity of the radiation is about 50 mJ/cm$^2$ to 10 J/cm$^2$, preferably about 500 mJ/cm$^2$ to 5 J/cm$^2$.

The UV radiation used herein may be any UV radiations polarized by passing through or being reflected from (a) a polarizer using a dielectric anisotropic coating on the surface of a transparent substrate such as quartz glass, soda-lime glass, soda-lime-free glass, or the like; (b) a polarizer with fine aluminum or other metallic wires; or (c) a Brewster polarizer using reflection from quartz glass.

The substrate temperature during UV irradiation is preferably the room temperature. Under circumstances, the substrate may be heated at 100° C. or below during UV irradiation. Preferably, the final film thus obtained from the above-described steps has a thickness of 30 to 1,000 μm.

The above-described method is adopted to form an alignment film and a liquid crystal film on the alignment film, completing a liquid crystal retardation film according to a typical method. The use of the photoreactive polymer in the alignment film enables the alignment film to have good interactions with liquid crystal molecules, achieving effective photo-alignment.

The alignment film or the liquid crystal retardation film is applicable to optical films or filters used to create stereoscopic images.

In accordance with still further another embodiment of the present invention, there is provided a display device comprising the alignment film. The display device may be a liquid crystal display device comprising the alignment film for liquid crystal alignment; or a stereoscopic imaging display device included in optical films or filters for realizing stereoscopic images. The constituent components of the display device are the same as those of a typical display device, excepting that the photoreactive polymer and the alignment film are included, and will not be described any more in further detail.

In the following are set forth preferred examples of the present invention for better understanding of the present invention. It is to be understood that the examples are only for illustrative purposes and are not intended to limit the scope of the present invention.

In the set forth examples, all the works dealing with compounds susceptible to air or water were carried out using dry-box or standard Schlenk techniques. The nuclear magnetic resonance (NMR) spectra were acquired using a Bruker 300 spectrometer, where $^1$H NMR and $^{13}$C NMR measurements were conducted at 75 MHz. The molecular weight and the molecular weight distribution of the polymer obtained by ring-opening hydrogenation were determined using gel permeation chromatography (GPC), which employed a polystyrene sample as a reference.

For purification, toluene was distilled in potassium/benzophenone, and dichloromethane was distilled in CaH$_2$.

Preparation Example 1

Preparation of

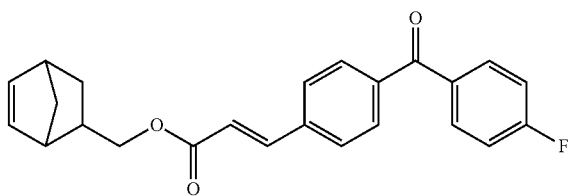 [SMILES: O=C(/C=C/c1ccc(C(=O)c2ccc(F)cc2)cc1)OCC1CC2C=CC1C2]

In a flask were placed a compound (116.2 g, 0.43 mol, Fw=270.26) represented by

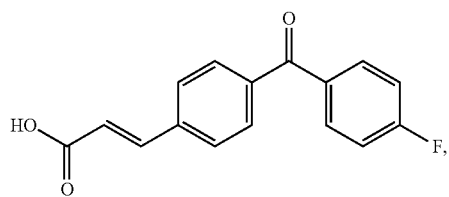 [SMILES: O=C(O)/C=C/c1ccc(C(=O)c2ccc(F)cc2)cc1]

N-(3-dimethylaminopropyl)-N'-ethylcarbodiimide hydrochloride (EDCI, 206 g, 1.08 mol), N,N-dimethylamidopyridine (DMAP, 10.5 g, 0.09 mol), and CH$_2$Cl$_2$ (1,500 ml). Diisopropylethylamine (DIPEA, 225 ml, 1.29 mol) and 5-norbornene-2-methanol (106.8 g, 0.86 mol, Fw=124.18) were added to the flask, which was then stirred at the room temperature for 20 hours. After completion of the reaction, water was added and the organic phase was extracted from water. The organic phase was washed with saline water and dried over magnesium sulfate. Then, the organic phase was filtered and purified by column chromatography (EA:Hex=1:7) to obtain 74.5 g of the target compound (yield: 46%, Fw=376.43, purity (GC): 98%).

1H-NMR (300 MHz, CDCl3): δ 7.90-7.71 (m, 5H), 7.64 (d, 2H), 7.22-7.14 (m, 2H), 6.55 (d, 1H), 6.17~5.98 (m, 2H), 4.10~3.76 (m, 2H), 2.94~2.75 (m, 2H), 2.45 (m, 1H), 1.91~1.83 (m, 1H), 1.48~1.16 (m, 2H), 0.59 (m, 1H)

Preparation Example 2

Preparation of

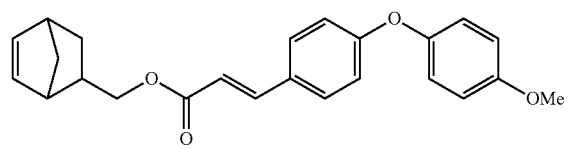 [SMILES: COc1ccc(Oc2ccc(/C=C/C(=O)OCC3CC4C=CC3C4)cc2)cc1]

In a flask were placed a compound (116.2 g, 0.43 mol, Fw=270.29) represented by

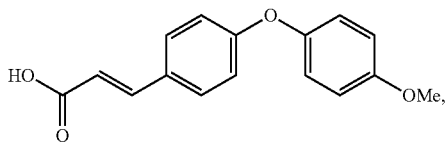 [SMILES: COc1ccc(Oc2ccc(/C=C/C(=O)O)cc2)cc1]

N-(3-dimethylaminopropyl)-N'-ethylcarbodiimide hydrochloride (EDCI, 206 g, 1.08 mol), N,N-dimethylamidopyridine (DMAP, 10.5 g, 0.09 mol), and CH$_2$Cl$_2$ (1,500 ml). Diisopropylethylamine (DIPEA, 225 ml, 1.29 mol) and 5-norbornene-2-methanol (106.8 g, 0.86 mol, Fw=124.18) were added to the flask, which was then stirred at the room temperature for 20 hours. After completion of the reaction, water was added and the organic phase was extracted from water. The organic phase was washed with saline water and dried over magnesium sulfate. Then, the organic phase was filtered and purified by column chromatography (EA:Hex=1:7) to obtain 84.2 g of the target compound (yield: 52%, Fw=376.46, purity (GC): 98%).

1H-NMR (300 MHz, CDCl3): δ 7.71-7.66 (m, 3H), 7.22-7.14 (m, 4H), 7.02 (s, 2H), 6.45 (d, 1H), 6.18~5.98 (m, 2H), 4.10~3.75 (m, 2H), 3.82 (s, 3H), 2.94~2.75 (m, 2H), 2.45 (m, 1H), 1.91~1.83 (m, 1H), 1.48~1.15 (m, 2H), 0.59 (m, 1H)

Preparation Example 3

Preparation of

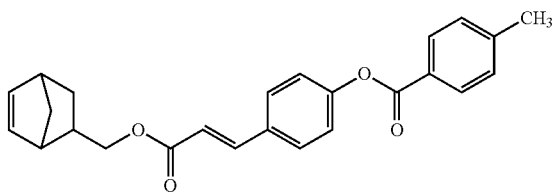 [SMILES: Cc1ccc(C(=O)Oc2ccc(/C=C/C(=O)OCC3CC4C=CC3C4)cc2)cc1]

In a flask were placed a compound (9.15 g, 32.4 mmol, Fw=282.30) represented by

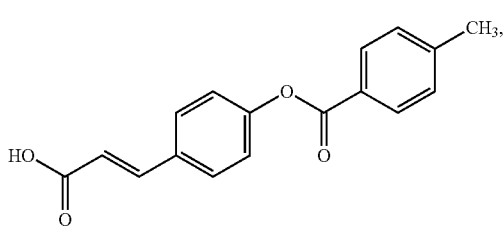 [SMILES: Cc1ccc(C(=O)Oc2ccc(/C=C/C(=O)O)cc2)cc1]

5-norbornene-2-methanol (4.82 g, 38.9 mmol, Fw=124.18), zirconium acetate hydroxide (0.1 g, 1 wt. %) and xylene (30 ml). Then azeotropic reflux was conducted at 180° C. in the nitrogen atmosphere for about 24 hours. After completion of the reaction, the temperature was lowered to the room temperature, and 100 vol. % of ethyl acetate was added. Extracted with 1M HCl and washed with water once more, the organic phase was dried over magnesium sulfate and removed of the solvent to obtain a very sticky liquid. The crude product was then purified by column chromatography (EA:Hex=1:10) to obtain 8.05 g of the target compound (yield: 64%, Fw=388.47, purity (GC): 98%).

1H-NMR (300 MHz, CDCl3): δ 7.84-7.71 (m, 5H), 7.35 (d, 2H), 7.23-7.14 (m, 2H), 6.55 (d, 1H), 6.17~5.98 (m, 2H), 4.10~3.76 (m, 2H), 2.94~2.75 (m, 2H), 2.45 (m, 1H), 2.22 (s, 3H), 1.91~1.83 (m, 1H), 1.48~1.16 (m, 2H), 0.59 (m, 1H)

Preparation Example 4

Preparation of

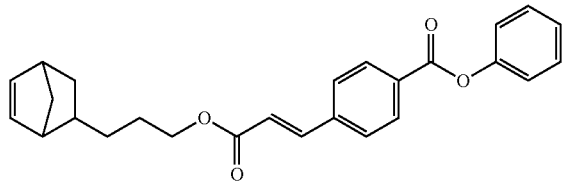 [SMILES: O=C(/C=C/c1ccc(C(=O)Oc2ccccc2)cc1)OCCCC1CC2C=CC1C2]

In a flask were placed a compound (9.15 g, 34.1 mmol, Fw=268.27) represented by

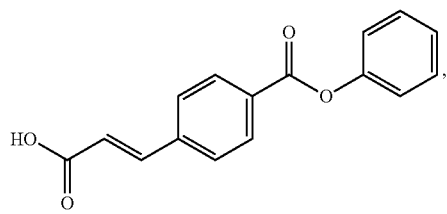 [SMILES: O=C(O)/C=C/c1ccc(C(=O)Oc2ccccc2)cc1]

5-norbornene-2-methanol (4.82 g, 31.7 mmol, Fw=152.24), zirconium acetate hydroxide (0.1 g, 1 wt. %) and xylene (30 ml). Then azeotropic reflux was conducted at 180° C. in the nitrogen atmosphere for about 24 hours. After completion of the reaction, the temperature was lowered to the room temperature, and 100 vol. % of ethyl acetate was added. Extracted with 1M HCl and washed with water once more, the organic phase was dried over magnesium sulfate and removed of the solvent to obtain a sticky liquid. The crude product was then purified by column chromatography (EA:Hex=1:10) to obtain 9.47 g of the target compound (yield: 69%, Fw=402.49, purity (GC): 97.5%).

1H-NMR (300 MHz, CDCl3): δ 7.84-7.71 (m, 5H), 7.35 (d, 2H), 7.23-7.14 (m, 2H), 6.55 (d, 1H), 6.17~5.98 (m, 2H), 5.0~4.9 (m, 2H), 2.94~2.75 (m, 2H), 2.45 (m, 1H), 1.91~1.83 (m, 1H), 1.48~1.16 (m, 2H), 0.59 (m, 1H)

Example 1

Polymerization of

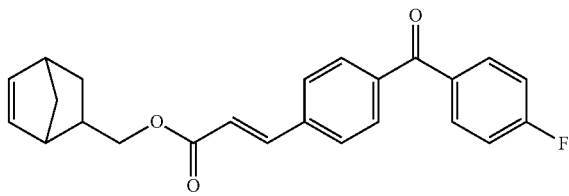 [SMILES: O=C(/C=C/c1ccc(C(=O)c2ccc(F)cc2)cc1)OCC1CC2C=CC1C2]

In a 250 ml Schlenk flask were placed 1.13 g of a compound (3 mmol, Fw=376.43) as a monomer represented by

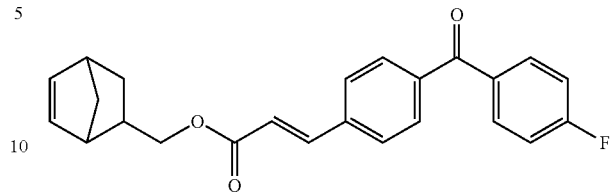

and 3 ml of purified toluene as a solvent. To the flask were added 6.73 mg of Pd(OAc)₂ and 7.76 mg of tricyclohexylphosphine in 1 ml of dichloromethane as a catalyst and 6.53 mg of dimethylanilinium tetrakiss(pentafluorophenyl)borate as a cocatalyst. The mixture was stirred at 90° C. for 18 hours to bring about a reaction.

After an elapse of 18 hours, the reactants were put in an excess of ethanol to obtain a white polymer precipitate. The precipitate was filtered out through a glass funnel to collect a polymer, which was then dried in a vacuum oven at 60° C. for 24 hours to yield 1.0 g of a final polymer product (Mw=170,000, PDI=3.2, yield=88%).

Example 2

Polymerization of

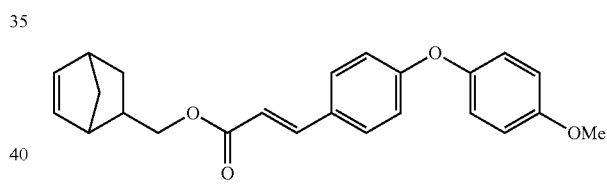

In a 250 ml Schlenk flask were placed 3.0 g of a compound (6.69 mmol) as a monomer represented by

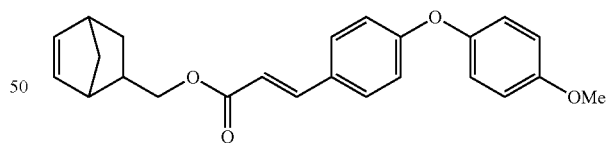

and 6 ml of purified toluene as a solvent. To the flask were added 0.62 mg of Pd(OAc)₂ and 0.71 mg of tricyclohexylphosphine in 1 ml of dichloromethane as a catalyst and 0.60 mg of dimethylanilinium tetrakiss(pentafluorophenyl)borate as a cocatalyst. The mixture was stirred at 90° C. for 18 hours to bring about a reaction.

After an elapse of 18 hours, the reactants were put in an excess of ethanol to obtain a white polymer precipitate. The precipitate was filtered out through a glass funnel to collect a polymer, which was then dried in a vacuum oven at 60° C. for 24 hours to yield 2.6 g of a final polymer product (Mw=124,000, PDI=2.9, yield=87%).

Example 3

Polymerization of

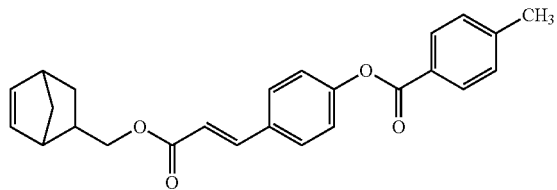 [SMILES: Cc1ccc(C(=O)Oc2ccc(/C=C/C(=O)OCC3CC4C=CC3C4)cc2)cc1]

In a 250 ml Schlenk flask were placed 1.17 g of a compound (3 mmol) as a monomer represented by

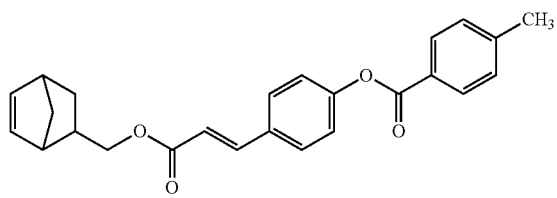 [SMILES: Cc1ccc(C(=O)Oc2ccc(/C=C/C(=O)OCC3CC4C=CC3C4)cc2)cc1]

and 3 ml of purified toluene as a solvent. To the flask were added 6.73 mg of Pd(OAc)$_2$ and 7.76 mg of tricyclohexylphosphine in 1 ml of dichloromethane as a catalyst and 6.53 mg of dimethylanilinium tetrakiss(pentafluorophenyl)borate as a cocatalyst. The mixture was stirred at 90° C. for 18 hours to bring about a reaction.

After an elapse of 18 hours, the reactants were put in an excess of ethanol to obtain a yellowish polymer precipitate. The precipitate was filtered out through a glass funnel to collect a polymer, which was then dried in a vacuum oven at 60° C. for 24 hours to yield 0.89 g of a final polymer product (Mw=103,000, PDI=3.6, yield=79%).

Example 4

Polymerization of

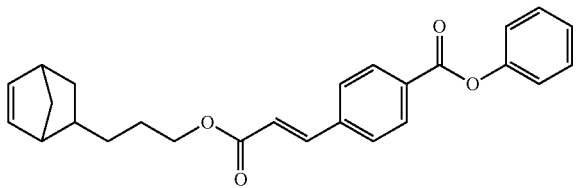 [SMILES: O=C(/C=C/c1ccc(C(=O)Oc2ccccc2)cc1)OCCCC1CC2C=CC1C2]

In a 250 ml Schlenk flask were placed 1.2 g of a compound (3 mmol, Fw=402.49) as a monomer represented by

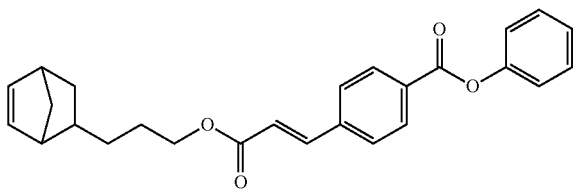 [SMILES: O=C(/C=C/c1ccc(C(=O)Oc2ccccc2)cc1)OCCCC1CC2C=CC1C2]

and 3 ml of purified toluene as a solvent. To the flask were added 6.73 mg of Pd(OAc)$_2$ and 7.76 mg of tricyclohexylphosphine in 1 ml of dichloromethane as a catalyst and 6.53 mg of dimethylanilinium tetrakiss(pentafluorophenyl)borate as a cocatalyst. The mixture was stirred at 90° C. for 18 hours to bring about a reaction.

After an elapse of 18 hours, the reactants were put in an excess of ethanol to obtain a yellowish polymer precipitate. The precipitate was filtered out through a glass funnel to collect a polymer, which was then dried in a vacuum oven at 60° C. for 24 hours to yield 1.01 g of a final polymer product (Mw=143,000, PDI=3.4, yield=84%).

Example 5

Preparation of Photoreactive Polymer by Ring-Opening Polymerization and Hydrogenation Reaction In a 250 ml Schlenk flask in the Ar atmosphere were placed 6.20 g (50 mmol) of 5-norbornene-2-methanol and then 34 g of purified toluene as a solvent. With the flask maintained at a polymerization temperature of 80° C., 11.4 mg (1.0 mmol) of triethyl aluminum was added as a cocatalyst. Subsequently, to the flask was added 1 ml (WCl$_6$: 0.01 mmol, ethanol: 0.03 mmol) of a 0.01 M (mol/L) toluene solution containing a mixture of tungsten hexachloride (WCl$_6$) and ethanol at a mixing ratio of 1:3. Finally, 0.84 g (7.5 mmol) of 1-octene as a molecular weight modifier was added to the flask, which was then stirred at 80° C. for 18 hours to bring about a reaction. After completion of the reaction, a small amount of ethyl vinyl ether as a polymerization inhibitor was added dropwise to the polymerization solution, and the flask was stirred for 5 minutes.

With the polymerization solution transferred to a 300 mL high-pressure reactor, 0.06 ml of triethyl aluminum (TEA) was added to the solution. Subsequently, 0.50 g of grace raney nickel (slurry phase in water) was added, and the solution was stirred at 150° C. for 2 hours under the hydrogen pressure maintained at 80 atm to bring about a reaction. After completion of the reaction, the polymerization solution was added dropwise to acetone to cause precipitation. The precipitate thus obtained was filtered out and dried in a vacuum oven at 70° C. for 15 hours, thereby obtaining 5.62 g of a ring-opened hydrogenated polymer of 5-norbornene-2-methanol (yield=90.6%, Mw=69,900, PDI=4.92).

In a 250 ml two-neck flask were placed the ring-opened hydrogenated polymer of 5-norbornene-2-methanol (15 g, 0.121 mol), triethylamine (Aldrich, 61.2 g, 0.605 mol), and THF (50 ml). Then, the flask was stirred in an ice-water bath at 0° C. 4-benzoyl cinnamoyl chloride (36.0 g, 0.133 mol, Fw=270.72) represented by

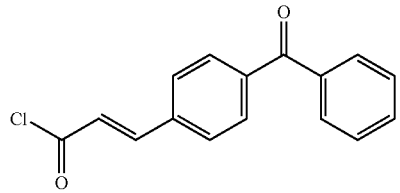 [SMILES: O=C(Cl)/C=C/c1ccc(C(=O)c2ccccc2)cc1]

was dissolved in 60 ml of THF, and the solution was added gradually using an additional flask. After an elapse of 10 minutes, the reactants were warmed to the room temperature and stirred for 18 more hours. The solution was diluted with ethyl acetate, transferred to a separatory funnel, and washed with water and NaHCO$_3$ several times. The reaction solution was added dropwise to acetone to cause precipitation. The resultant precipitate was filtered out and dried in a vacuum oven at 70° C. for 15 hours to give a ring-opened hydrogenated polymer of 5-norbornene-2-methyl-4'-benzoyl cinnamate (yield=93%).

Example 6

Copolymerization of

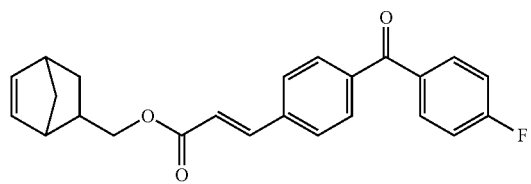 and

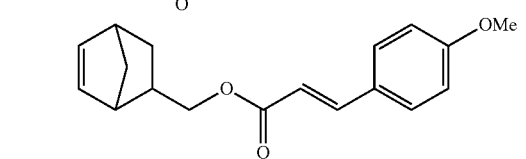

In a 250 ml Schlenk flask were placed 0.34 g (1.2 mmol, Fw=284.36) of

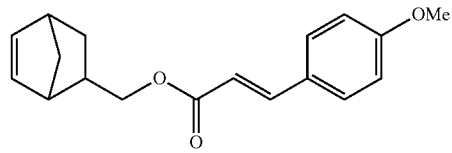 [SMILES: COc1ccc(/C=C/C(=O)OCC2CC3C=CC2C3)cc1]

and 0.903 g (2.4 mmol, Fw=376.43) of

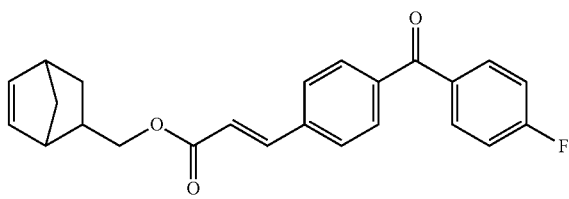 [SMILES: O=C(/C=C/c1ccc(C(=O)c2ccc(F)cc2)cc1)OCC1CC2C=CC1C2]

as monomers, and 3 ml of purified toluene as a solvent. To the flask were added 6.73 mg of Pd(OAc)$_2$ and 7.76 mg of tricyclohexylphosphine in 1 ml of dichloromethane as a catalyst and 6.53 mg of dimethylanilinium tetrakiss(pentafluorophenyl)borate as a cocatalyst. The mixture was stirred at 90° C. for 18 hours to bring about a reaction.

After an elapse of 18 hours, the reactants were put in an excess of ethanol to obtain a white polymer precipitate. The precipitate was filtered out through a glass funnel to collect a polymer, which was then dried in a vacuum oven at 60° C. for 24 hours to yield 1.07 g of a final polymer product (Mw=130,000, PDI=4.2, yield=86%).

Example 7

Copolymerization of

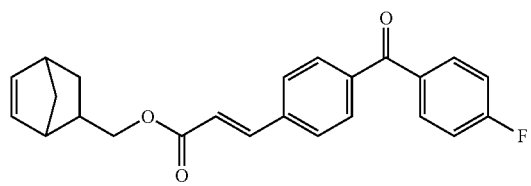 and

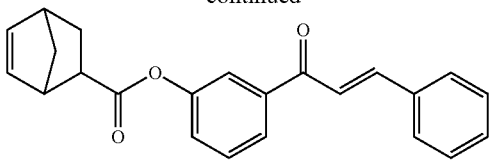

In a 250 ml Schlenk flask were placed 0.41 g (1.2 mmol, Fw=344.41) of

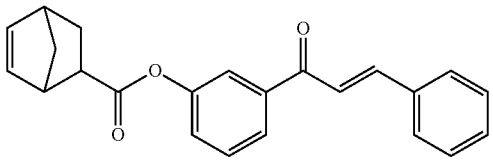 [SMILES: O=C(/C=C/c1ccccc1)c1cccc(OC(=O)C2CC3C=CC2C3)c1]

and 0.903 g (2.4 mmol, Fw=376.43) of

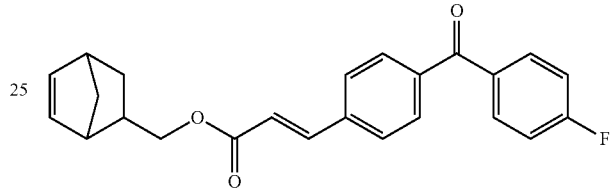

as monomers, and 3 ml of purified toluene as a solvent. To the flask were added 6.73 mg of Pd(OAc)$_2$ and 7.76 mg of tricyclohexylphosphine in 1 ml of dichloromethane as a catalyst and 6.53 mg of dimethylanilinium tetrakiss(pentafluorophenyl)borate as a cocatalyst. The mixture was stirred at 90° C. for 18 hours to bring about a reaction.

After an elapse of 18 hours, the reactants were put in an excess of ethanol to obtain a white polymer precipitate. The precipitate was filtered out through a glass funnel to collect a polymer, which was then dried in a vacuum oven at 60° C. for 24 hours to yield 1.06 g of a final polymer product (Mw=80,000, PDI=3.6, yield=81%).

Comparative Example 1

Polymerization of

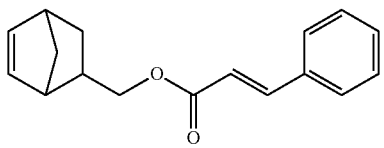 [SMILES: O=C(/C=C/c1ccccc1)OCC1CC2C=CC1C2]

In a 250 ml Schlenk flask were placed 0.251 g (0.6 mmol, Fw=254.33) of

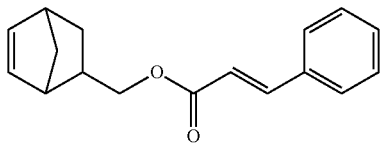 [SMILES: O=C(/C=C/c1ccccc1)OCC1CC2C=CC1C2]

as a monomer and 3 ml of purified toluene as a solvent. To the flask were added 6.73 mg of Pd(OAc)$_2$ and 7.76 mg of tricyclohexylphosphine in 1 ml of dichloromethane as a catalyst and 6.53 mg of dimethylanilinium tetrakiss(pentafluorophenyl)borate as a cocatalyst. The mixture was stirred at 90° C. for 18 hours to bring about a reaction.

After an elapse of 18 hours, the reactants were put in an excess of ethanol to obtain a white polymer precipitate. The precipitate was filtered out through a glass funnel to collect a polymer, which was then dried in a vacuum oven at 60° C. for 24 hours to yield 0.99 g of a final polymer product (Mw=130,000, PDI=4.2, yield=86%).

Preparation Example 5

Preparation of Liquid Crystal Film

The individual photoreactive polymers synthesized in Examples 1 and 2 and Comparative Example 1 were used to fabricate liquid crystal films. Each photoreactive polymer was dissolved in c-pentanone solvent at a concentration of 2 wt. %, applied onto a 80 micron thick polyethylene terephthalate (SH71 manufactured by SKC, Inc. in South Korea) substrate by the roll coating technique to have a thickness of 1,000 Å after drying. Then, the substrate was heated in an oven at 80° C. for 3 minutes to eliminate the solvent from the coating film, thereby providing the final coating film.

The exposure was conducted with a high-pressure mercury lamp having an intensity of 200 mW/cm$^2$ as a light source and a wire-grid polarizer (Moxtek Inc.) to generate UV rays vertically polarized with respect to the lengthwise direction of the film. The polarized UV rays were irradiated on the coating film for 5 seconds to cause alignment, thereby forming an alignment film.

Subsequently, a polymerizable reactive liquid crystal solution was prepared by dissolving a solid mixture including 95.0 wt. % of UV-polymerization cyano biphenyl acrylate and 5.0 wt. % of Irgacure 907 (Ciba-Geigy Chemical Corp.) as a photo-initiator in toluene to contain 25 parts by weight of liquid crystals with respect to 100 parts by weight of the liquid crystal solution.

The liquid crystal solution thus obtained was applied on the alignment film by the roll coating technique to have a thickness of 1 μm after drying, and then dried at 80° C. for 2 minutes to have the liquid crystal molecules aligned. The aligned liquid crystal film was exposed to unpolarized UV radiation from a high-pressure mercury lamp having an intensity of 200 mW/cm$^2$ used as a light source to stabilize the alignment status of the liquid crystals, thereby preparing a retardation film.

The alignment for the retardation film was evaluated and compared by measuring light leakage ["빛샘"] between two polarizers in terms of transmittance, and the quantitative phase difference value was measured using an Axoscan (Axomatrix).

Experimental Example 1

Evaluation of Alignment (Light Leakage)

To evaluate the alignment of the alignment film, the liquid crystal retardation film obtained in Preparation Example 5 using each of the photoreactive polymers of Examples 1 and 2 and Comparative Example 1 was observed with a polarized microscope between two vertically arranged polarizers. The alignment was rated in terms of integer numbers from 1 to 5, the highest number, 5 indicating the best alignment.

As for the measurement of light leakage in terms of transmittance, 80 micron thick polyethylene terephthalate (SH71 manufactured by SKC, Inc. in South Korea) was used as a reference. With the liquid crystal retardation film disposed between two vertically arranged polarizers, a polarized microscope was used to determine the transmittance of an incident light passing through the polarizers and the retardation film. The measurement results of the phase difference value as well as the evaluation of alignment in terms of light leakage are presented in Table 1.

TABLE 1

| Photoreactive Polymer in Alignment Film | Alignment (Increasing from 0 to 5) | Liquid Crystal Thickness | Phase Difference Value |
|---|---|---|---|
| Example 1 | 5 | 1 μm | 129 nm |
| Example 2 | 5 | 1 μm | 125 nm |
| Comparative Example 1 | 3 | 1 μm | 103 nm |

* In the alignment evaluation, UV curing was conducted on the respective alignment films with a constant amount of light at 100 mJ/cm$^2$, to cause liquid crystal alignment; and
* In determination of the phase difference value, a light source with a wavelength of 550 nm was used to measure the phase difference value in the plane direction of the film.

Referring to Table 1, the retardation films formed from the polymers of Examples 1 and 2 exhibited a uniform liquid crystal alignment direction irrespective of the wavelength of the incident light, consequently with good alignment, and had an in-film phase difference value in the range of 129 nm to 125 nm to realize excellent anisotropic properties of liquid crystals.

Contrarily, the retardation film formed from the polymer of Comparative Example 1 showed a deterioration in the alignment with fluctuations of the liquid crystal alignment direction and had a low phase difference value even at the same liquid crystal thickness of the retardation films using the polymers of Examples 1 and 2, consequently with poor anisotropic properties.

What is claimed is:

1. A photoreactive polymer comprising a repeating unit represented by the following formula 2a or 2b,
  wherein the photoreactive polymer comprising the repeating unit of the formula 2a has a weight average molecular weight of 80,000 to 170,000:

[Formula 2a]

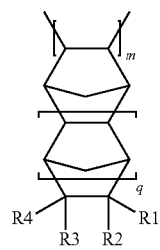

[Formula 2b]

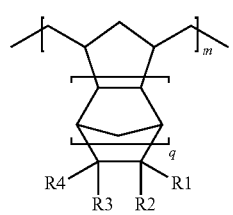

wherein in the formulas 2a and 2b, independently, m is 50 to 5,000;
q is an integer from 0 to 4; and
at least one of R1, R2, R3 and R4 is a radical represented by the following formula 1a, among the R1 to R4, the remainders other than the radical of the formula 1a are the same as or different from one another and independently selected from the group consisting of hydrogen; halogen; substituted or unsubstituted linear or branched alkyl having 1 to 20 carbon atoms; substituted or unsubstituted linear or branched alkenyl having 2 to 20 carbon atoms; substituted or unsubstituted linear or branched alkynyl having 2 to 20 carbon atoms; substituted or unsubstituted cycloalkyl having 3 to 12 carbon atoms; substituted or unsubstituted aryl having 6 to 40 carbon atoms; substituted or unsubstituted arylalkyl having 5 to 12 carbon atoms; and a polar functional group comprising at least one of oxygen, nitrogen, phosphor, sulfur, silicon, and boron;

when the R1 to R4 are not hydrogen, halogen, or a polar functional group, at least one of a R1 and R2 coordination and a R3 and R4 coordination is bonded to each other to form an alkylidene group having 1 to 10 carbon atoms; or R1 or R2 is bonded to either R3 or R4 to form a saturated or unsaturated aliphatic ring having 4 to 12 carbon atoms or an aromatic ring having 6 to 24 carbon atoms,

[Formula 1a]

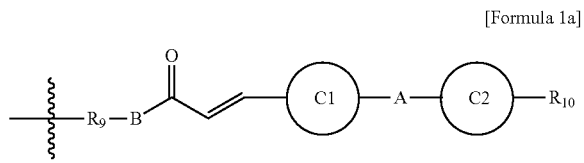

wherein A is selected from the group consisting of oxygen, sulfur, —NH—, substituted or unsubstituted alkylene having 1 to 20 carbon atoms, carbonyl, —(O=)C—O—, —O—C(=O)—, and —CONH—;

B is chemical bond, oxygen, sulfur, —NH—, or 1,4-phenylene; R9 is substituted or unsubstituted alkylene having 1 to 20 carbon atoms;

C1 is C6-C40 arylene unsubstituted or substituted with at least one functional group selected from the group consisting of halogen, cyano, and nitro; C7-C15 arylalkylene unsubstituted or substituted with at least one functional group selected from halogen, cyano, and nitro; or C4-C40 heteroarylene comprising a heteroelement in Group 14, 15 or 16;

C2 is C6-C40 arylene unsubstituted or substituted with at least one functional group selected from the group consisting of halogen, cyano, and nitro; or C4-C40 heteroarylene comprising a heteroelement in Group 14, 15 or 16; and R10 is selected from the group consisting of halogen; cyano; nitro; —NCS; substituted or unsubstituted linear or branched alkyl having 1 to 20 carbon atoms; substituted or unsubstituted alkoxy having 1 to 20 carbon atoms; substituted or unsubstituted aryloxy having 6 to 30 carbon atoms; and substituted or unsubstituted aryl having 6 to 40 carbon atoms.

2. The photoreactive polymer as claimed in claim 1, wherein the photoreactive polymer comprising the repeating unit of formula 2b has a weight average molecular weight of 69,900 to 1,000,000.

3. The photoreactive polymer as claimed in claim 1, wherein the polar functional group comprising at least one of oxygen, nitrogen, phosphor, sulfur, silicon, and boron is selected from the group consisting of the following functional groups:

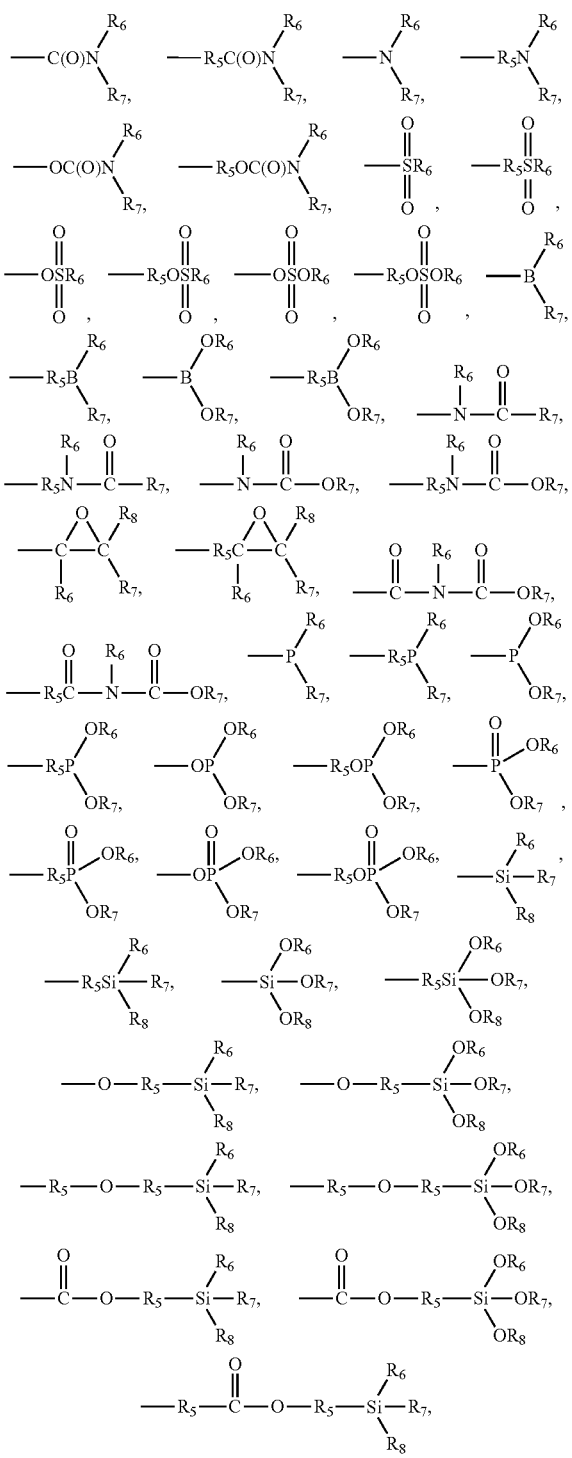

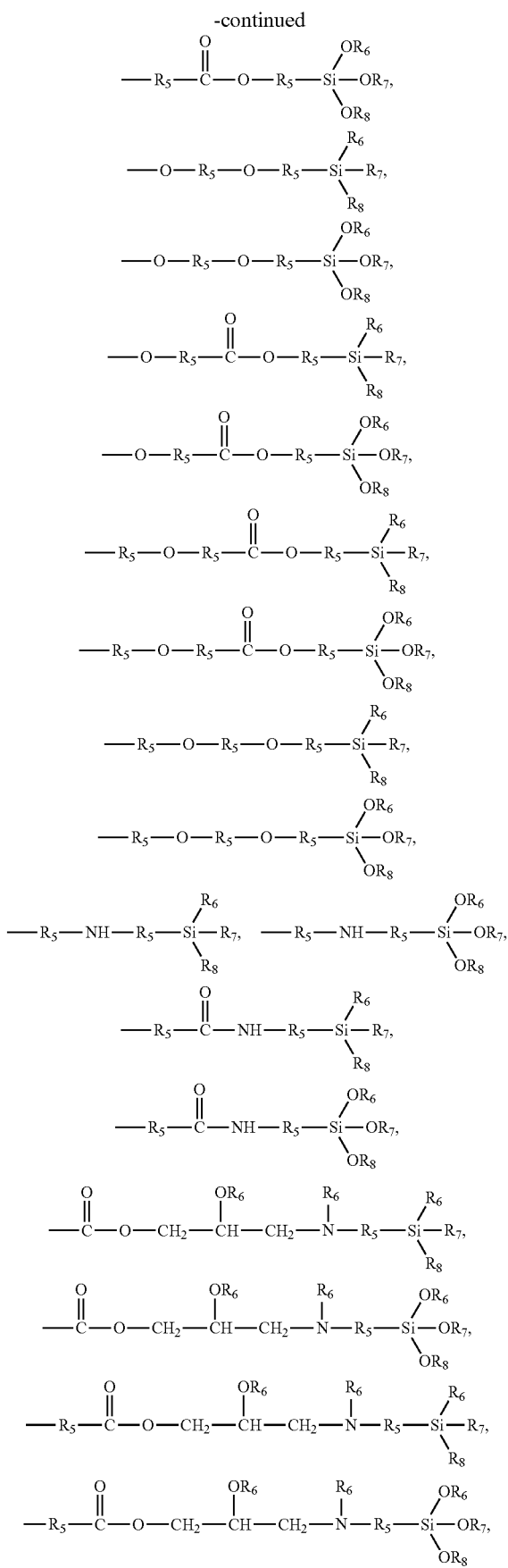

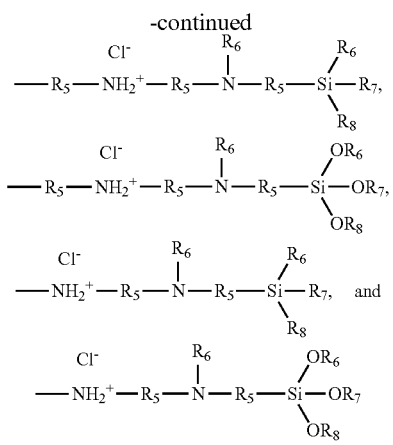

wherein p is independently an integer from 1 to 10;
R5 is substituted or unsubstituted linear or branched alkylene having 1 to 20 carbon atoms; substituted or unsubstituted linear or branched alkenylene having 2 to 20 carbon atoms; substituted or unsubstituted linear or branched alkynylene having 2 to 20 carbon atoms; substituted or unsubstituted cycloalkylene having 3 to 12 carbon atoms; substituted or unsubstituted arylene having 6 to 40 carbon atoms; substituted or unsubstituted carbonyloxylene having 1 to 20 carbon atoms; or substituted or unsubstituted alkoxylene having 1 to 20 carbon atoms; and
R6, R7 and R8 are independently selected from the group consisting of hydrogen; halogen; substituted or unsubstituted linear or branched alkyl having 1 to 20 carbon atoms; substituted or unsubstituted linear or branched alkenyl having 2 to 20 carbon atoms; substituted or unsubstituted linear or branched alkynyl having 2 to 20 carbon atoms; substituted or unsubstituted cycloalkyl having 3 to 12 carbon atoms; substituted or unsubstituted aryl having 6 to 40 carbon atoms; substituted or unsubstituted alkoxy having 1 to 20 carbon atoms; and substituted or unsubstituted carbonyloxy having 1 to 20 carbon atoms.

4. A method for preparing the photoreactive polymer as claimed in claim 1, comprising:
performing an addition polymerization reaction using a monomer represented by the following formula 1 in the presence of a catalyst composition comprising a precatalyst comprising a transition metal in Group 10 and a cocatalyst to form a repeating unit of the formula 2a:

[Formula 1]

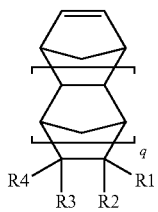

wherein q, R1, R2, R3 and R4 are as defined in the formula 2a.

5. A method for preparing the photoreactive polymer as claimed in claim 1, comprising:
performing a ring-opening polymerization reaction using a monomer represented by the following formula 1 in the presence of a catalyst composition comprising a precatalyst comprising a transition metal in Group 4, 6 or 8 and a cocatalyst to form a repeating unit of the formula 2b:

[Formula 1]

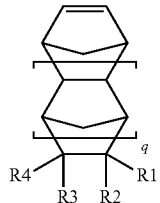

wherein q, R1, R2, R3 and R4 are as defined in the formula 2b.

6. The method as claimed in claim 5, wherein the ring-opening polymerization reaction comprises performing a hydrogenation reaction on a double bond of a norbornene ring included in the monomer of the formula 1.

7. An alignment film comprising the photoreactive polymer as claimed in claim 1.

8. A liquid crystal retardation film comprising the alignment film as claimed in claim 7 and a liquid crystal film on the alignment film.

9. A display device comprising the alignment film as claimed in claim 7.

10. An alignment film comprising the photoreactive polymer as claimed in claim 2.

11. An alignment film comprising the photoreactive polymer as claimed in claim 3.

* * * * *